United States Patent [19]

Williams

[11] Patent Number: 5,178,282

[45] Date of Patent: Jan. 12, 1993

[54] MODULAR SURGICAL PACKAGING SYSTEM

[75] Inventor: Rodger Williams, Arlington, Tex.

[73] Assignee: Alcon Surgical, Inc., Fort Worth, Tex.

[21] Appl. No.: 810,243

[22] Filed: Dec. 19, 1991

[51] Int. Cl.⁵ .............................................. B65D 69/00
[52] U.S. Cl. ................................... 206/570; 206/363; 206/370; 206/438; 206/440
[58] Field of Search ............... 206/225, 370, 438, 439, 206/440, 470, 570, 571, 572, 363, 803; 229/239, 235

[56] References Cited

U.S. PATENT DOCUMENTS

| | | |
|---|---|---|
| 1,316,612 | 9/1919 | Hay . |
| 1,436,406 | 11/1922 | Schulz .................. 206/440 |
| 2,062,973 | 12/1936 | Gluckstein . |
| 3,690,315 | 9/1972 | Chittenden et al. ................ 206/438 |
| 3,727,750 | 4/1973 | Petter ............................ 206/63.2 R |
| 3,954,174 | 5/1976 | Kraus ................................. 206/223 |
| 4,022,324 | 5/1977 | Schuster ........................... 206/439 |
| 4,113,109 | 9/1978 | Donnelli et al. ................ 211/49 R |
| 4,280,643 | 7/1981 | Cordova et al. ................... 206/225 |
| 4,522,302 | 6/1985 | Paikoff ............................... 206/570 |
| 4,523,679 | 6/1985 | Paikoff et al. ........................ 206/370 |
| 4,660,723 | 4/1987 | Dechirot ............................. 206/493 |
| 4,661,326 | 4/1987 | Schainholz ........................ 206/439 |
| 4,928,830 | 5/1990 | Brewer ............................... 206/438 |
| 5,040,680 | 8/1991 | Wilson et al. ....................... 206/438 |
| 5,060,814 | 10/1991 | Oglesbee ............................ 206/470 |
| 5,097,950 | 3/1992 | Weiss et al. ......................... 206/370 |

FOREIGN PATENT DOCUMENTS

WO81/01545 6/1981 PCT Int'l Appl. .

Primary Examiner—David T. Fidei
Attorney, Agent, or Firm—James A. Arno; Gregg C. Brown

[57] ABSTRACT

A modular surgical packaging system is shown which includes a central package with an open interior. The open interior is adapted to contain a first type of sterilizable surgical item. The external sidewalls of the central package have one or more accessory receiving compartments formed therein. One or more accessory modules, adapted to contain a second type of sterilizable surgical item, are received within the accessory receiving compartments formed on the external sidewalls of the central package in piggyback fashion.

5 Claims, 3 Drawing Sheets

MODULAR SURGICAL PACKAGING SYSTEM

BACKGROUND OF THE INVENTION

1. Field of the Invention

The present invention relates generally to a modular packaging system for packaging and organizing surgical items which must be contained under sterile conditions, and is particularly directed to such a packaging system for securely packaging surgical items which are sterilized by diverse means.

2. Description of the Prior Art

Modern surgical procedures require the use of a large variety of diverse items, all of which must be sterile. Common sterilization techniques include GAMMA irradiation, E Beam, ETO and steam, each of which has attendant advantages and disadvantages. For example, GAMMA irradiation is often preferred as a means of sterilization, since it is economical, absolute, and since products sterilized in such manner do not require sterility testing or post sterilization quarantine. The GAMMA irradiation technique does have certain disadvantages, however, including the tendency to discolor certain plastics and to physically degrade certain materials. Products which cannot be sterilized by GAMMA irradiation are typically sterilized either with ethylene oxide (ETO) or with steam.

The packaging of sterile surgical articles used in specific surgical procedures allows such articles to be maintained under aseptic conditions within the package during storage and organizes the commonly needed items specific to the surgical procedure at hand. For instance, most hospitals and outpatient surgery centers order the majority of their disposable products used in one surgical procedure in one package, sometimes referred to as a "procedure pack." The prior art packaging systems and methods have generally been designed to contain articles which may be sterilized by the same means within the same container. When it is desired to provide, in a single unit, diverse sterile articles which would require different methods of sterilization, the common practice is to package the diverse article separately.

In the area of ophthalmic surgical procedures, the present industry custom is to place a number of components, including products such as surgical drapes, surgical instruments and various adjunct pharmaceutical products in plastic bags. All of these products must be sterilized and maintained in a sterile condition prior to opening the package in which they are contained in the operating room. Since different types of sterilization are required in conjunction with different types of products, a large plastic bag containing surgical drapes and other products may need to be sterilized by means different from that utilized to sterilize an adjunct pharmaceutical product, such as a bottle of irrigating fluid. The present industry practice is to attach the adjunct pharmaceutical product or products in a separate bag which is taped or otherwise attached to the plastic bag containing the surgical drapes and associated products. This practice is referred to as "piggybacking."

There are a number of drawbacks to the present industry practice as previously described. Plastic bags containing surgical products are relatively cumbersome, and therefore difficult for operating room personnel to open and disassemble. Additionally, the present method of packaging does not allow for convenient storage, since large plastic bags containing products cannot be easily stored by means of stacking. Finally, plastic bags offer little, if any, protection for the contents of the bag from physical damage due to impact during shipping or other handling.

A need thus exists for a modular surgical packaging system for packaging various products utilized during surgical procedures which is an improvement upon the use of flexible plastic bags.

A need also exists for such a modular packaging system which provides a convenient method for packaging surgical products which are sterilizable by diverse means.

A need also exists for such a packaging system which more effectively organizes the components being packaged including surgical drapes, surgical instruments and various adjunct pharmaceutical products.

A need also exists for such a packaging system which can be stacked efficiently for convenient storage and which effectively protects the contents of the packaging system from physical damage during normal use and handling.

A need also exists for such a packaging system which is simple in design and economical to manufacture.

SUMMARY OF THE INVENTION

The modular surgical packaging system of the invention includes a central package having external sidewalls and an open interior. The open interior is adapted to contain a first type of sterilizable surgical item, the external sidewalls of the central package having at least one accessory receiving compartment formed therein. An accessory module adapted to contain a second type of sterilizable surgical item is received within the accessory receiving compartment formed on the external sidewalls of the central package.

Preferably, the open interior of the central package is adapted to contain surgical items which are sterilizable by a first means of bacteria sterilization, and the accessory module is adapted to contain surgical items which are sterilizable by one or more means of bacterial sterilization other than the first means of sterilization. Most preferably, the open interior of the central package is adapted to contain surgical items which are sterilizable by GAMMA irradiation. The accessory module is a piggyback module which is contained within a recessed compartment formed on the external sidewalls of the central package and is adapted to contain surgical items which are sterilizable by diverse means of bacterial sterilization, such as through the use of a sterilization gas such as ethylene oxide or steam.

The accessory module can assume various shapes, depending upon the particular shape of the accessory to be accommodated. Where the shape of the accessory is that of a liquid bottle, the accessory module can be provided as a container having an accessory receiving body and a hinged lid, the body being shaped to generally conform to a recessed compartment formed on the external sidewalls of the central package. For example, the accessory receiving module can also be provided with a planar exterior portion and an associated sleeve. The sleeve is adapted to receive a liquid bottle for enclosing the bottle when the accessory module is received within a recessed compartment of the central package. The planar exterior portion is foldable along a central axis to conform to the shape of the external sidewalls of the central package when the module is received within a selected one of the recessed compartments.

The central package can also be provided with a handle having a handle opening, the handle opening being selectively sized to receive an outwardly extending projection extending from a vertically oriented storage panel, whereby a plurality of the modular packaging systems can be arranged on the storage panel for convenient access during surgical procedures.

Additional objects, features and advantages will be apparent in the written description which follows.

DETAILED DESCRIPTION OF THE INVENTION

Figure 1:
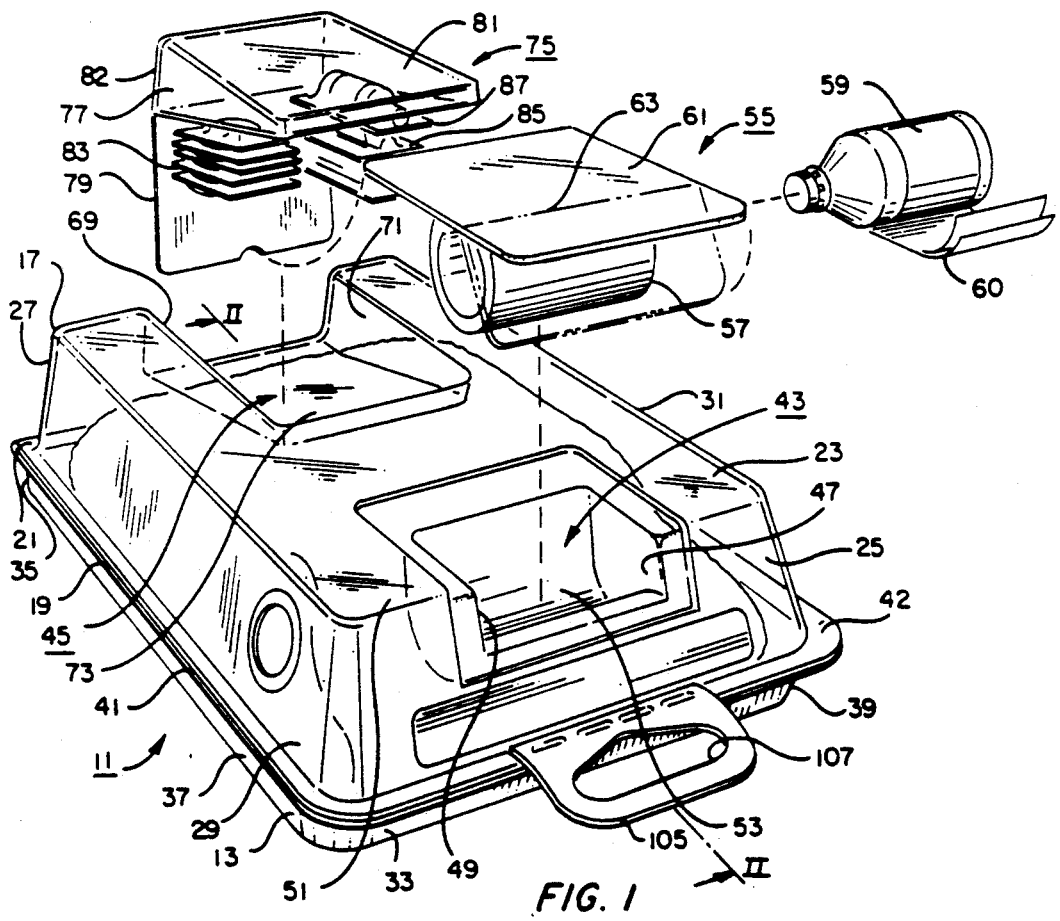
FIG. 1 is a perspective view of a modular surgical packaging system of the invention showing two accessory receiving compartments formed thereon and illustrating the assembly of a pair of accessory modules within the accessory receiving compartments.

FIG. 1 shows a modular surgical packaging system of the invention, designated generally as 11. The packaging system 11 includes a central package or core unit 13 having external sidewalls and an open interior (15 in FIG. 2). The assembled central package of the embodiment of the invention shown in FIG. 1 forms a generally rectangular body which can be conveniently manufactured from a variety of synthetic materials using known techniques. For instance, the central package 13 can be conveniently formed of polystyrene having upper and lower halves 17, 19 which are joined in clamshell fashion at a flexible rear hinge 21. The central package 13 can also be formed as discreet halves 18, 20, as shown in FIG. 3. The upper half 17 (FIG. 1) includes a generally planar top surface 23 and downwardly depending front, rear and opposing sidewalls, 25, 27, 29 and 31, respectively.

The lower half 19 of the central package 13 similarly includes front, rear and opposing sidewalls, 33, 35, 37 and 39, respectively, and is selectively sized to matingly engage the upper half 17 at a peripheral lip region 41. The peripheral lip region 41 comprises an outwardly extending flange which circumscribes the sidewalls of the lower half 19. The upper half 17 is provided with a similar and mating lip region 42 which overlays the lip region 41 of the lower half 19 in the closed position shown in FIG. 1. Although the central package 13 is shown having relatively rigid sidewalls in the preferred embodiment of FIGS. 1 and 2, it will be understood that the sidewalls of the central package could be manufactured of relatively soft or flexible materials, as well.

The central package 13 has at least one accessory receiving compartment formed therein. In the embodiment of FIG. 1, there are two accessory receiving compartments 43, 45 integrally formed within the external sidewalls of the central package 13. As will be explained more fully, the open interior 15 of the central package 13 is preferably adapted to contain surgical items which are sterilizable by first means of bacteria sterilization, most preferably by GAMMA irradiation. Surgical drapes and implements sterilizable by GAMMA irradiation can then be packaged within the open interior 15 with the sterile package being sealed along the peripheral lips 41,42. One or more accessory modules are mounted within the recessed accessory receiving compartments formed on the external sidewalls of the central package 13. The contents of the accessory modules 43, 45 are preferably sterilizable by diverse means of sterilization, such as by ethylene oxide or by steam. For instance, a rubber closured vial of medicament agent which is incompatible with GAMMA irradiation sterilization and which is heat sterilized separately can be placed within the respective accessory receiving compartment.

In the embodiment of the invention shown in FIG. 1, the accessory receiving compartment 43 is integrally formed, as by molding during the manufacture of the polystyrene package, and forms a recessed indentation in the generally planar top surface 23 of the container external sidewalls. The accessory receiving compartment 43 includes generally vertically extending sidewalls 47, 49 extending downwardly from the planar top surface 23 of the central package 13. The vertically extending sidewalls are connected by an arcuate floor region 53 which is arranged generally transverse to the longitudinal axis of the central package (illustrated as 51 in FIG. 3). The piggyback module 55 includes a sleeve member 57 which, in this case, is generally cylindrically shaped in order to hold a liquid container such as a bottle of irrigating fluid 59. The cylindrical exterior 59 of the sleeve 57 is sized to be received within the arcuate floor region 53 of the accessory receiving pocket 43 in mating fashion. Additional protective padding type materials 60 can circumscribe the container 59 to further protect fragile sterile items.

Figure 2:
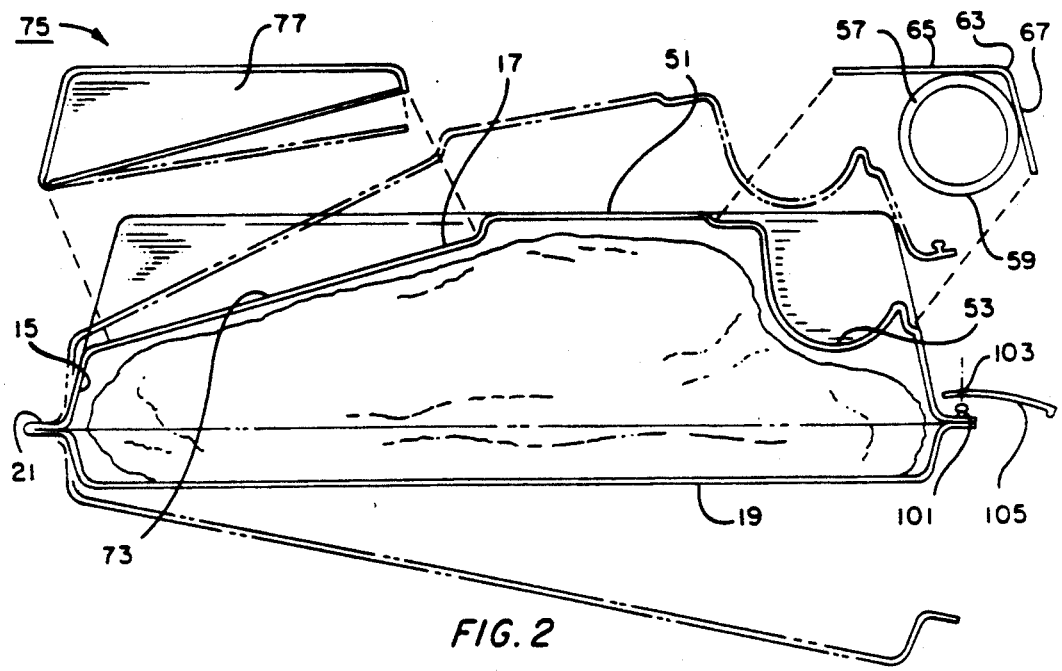
FIG. 2 is a side, cross-sectional view of the modular packaging system of FIG. 1 showing the central package thereof in the closed position in solid lines and showing the package in the open position in dotted lines and also illustrating the assembly of the accessory modules.
Figure 3:
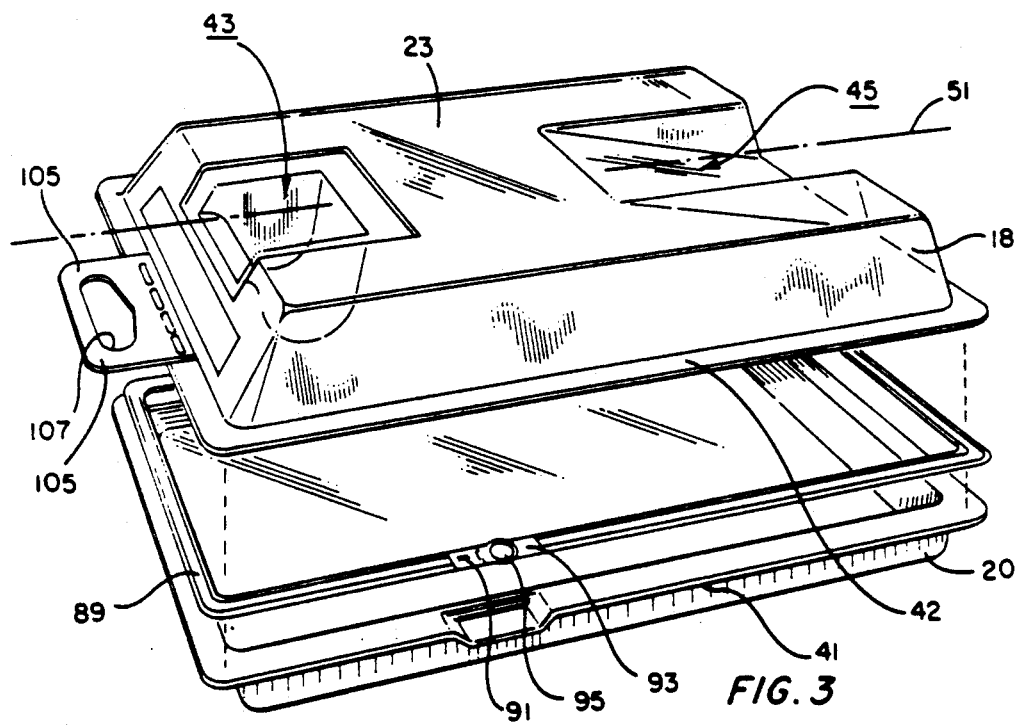
FIG. 3 is a side view of the top and bottom halves of the central package of the packaging system of FIG. 1 showing the assembly thereof.

Although the accessory module 55 is particularly adapted to receive a cylindrically shaped liquid container in the embodiment of the invention shown in FIGS. 1 and 2, it will be appreciated by those skilled in the art that the module can assume various shapes, i.e., oblong, square, rectangular, etc., depending upon the particular shape of the accessory to be accommodated.

The particular piggyback module 55 shown in FIG. 1 also has a planar exterior portion 61 associated with the sleeve member 57 which encloses the sleeve 57 and container 59 within the recessed compartment 43 of the central package 13. The planar exterior portion 61 is foldable along a central axis 63 to form a first planar fold 65 (FIG. 2) which lies generally in the plane of the top surface 23 of the central package 13 when the piggyback module is received within the accessory receiving compartment 43. The remainder of the planar exterior portion 61 forms a downwardly angled fold 67 which conforms to the shape of the external sidewalls of the central package and completes the enclosure within the accessory receiving compartment.

The second accessory receiving compartment 45, shown in FIG. 1, also includes generally vertically extending sidewalls 69, 71 which extend downwardly from the plane of the top surface 23 of the central package 13. The vertically extending sidewalls are connected by a sloped floor 73 which forms an opening of increasing depth in the direction of the rear sidewall 27 of the central package 13. When viewed from the side, as shown in FIG. 2, the sloped floor 73 forms a triangular indentation in the exterior sidewalls of the central container.

Figure 6:
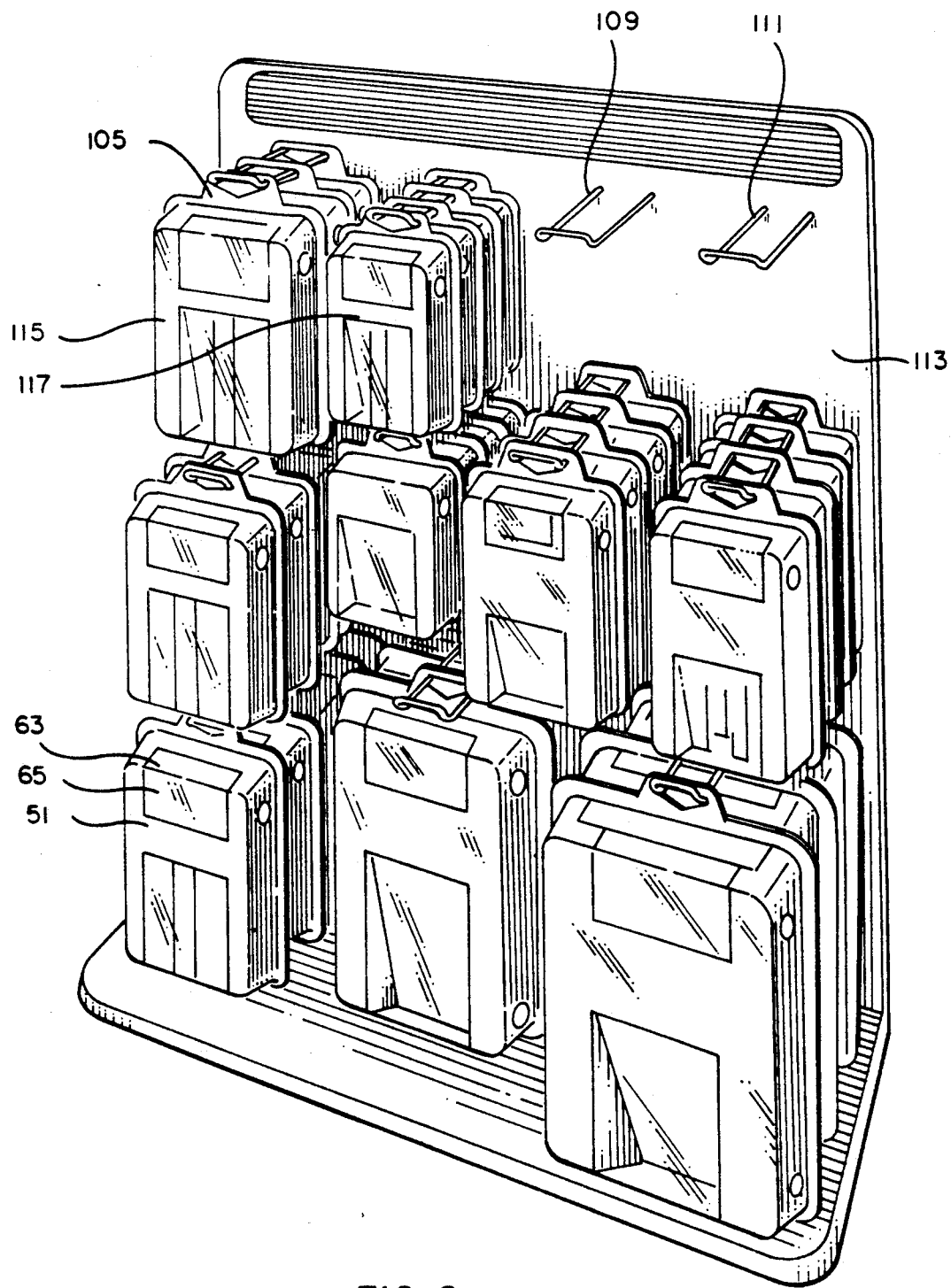
FIG. 6 is a perspective view of a vertically oriented storage panel having outwardly extending projections which are adapted to receive a plurality of the modular surgical packaging systems of the invention.

The piggyback module 75 is also provided having an accessory receiving body 77, in this case of triangular cross-section, and with a hinged lid 79. The module 75 assumes a generally triangular shape in external configuration when the lid 79 is closed, allowing the body 77 to be closely received within the accessory receiving compartment 45. In the assembled state, the top portion 81 of the module 75 is arranged generally coplanar with the plane of the top surface 23 of the central package 13. The rear wall 82 of the module conforms generally to the shape of the external sidewalls of the central package (best seen as 67 in FIG. 6). The module 75 is adapted to receive a variety of surgical items 83, 85, 87, certain of which are preferably sterilizable by a diverse form of sterilization than the components which are contained within the open interior 15 of the central package 13. For instance, if the components contained within the central package 13 are sterilized by GAMMA irradiation, the items contained within the module 75 are preferably sterilized by a means of sterilization other than irradiation.

Figure 4:
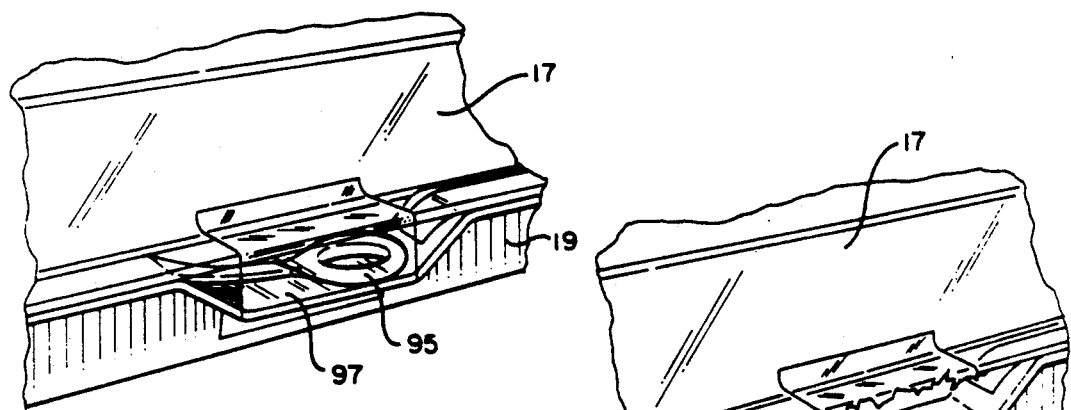
FIG. 4 is an enlarged view of a portion of the external sidewalls of the assembled central package showing the pull tab and sealant ribbon used to assemble the central package.
Figure 5:
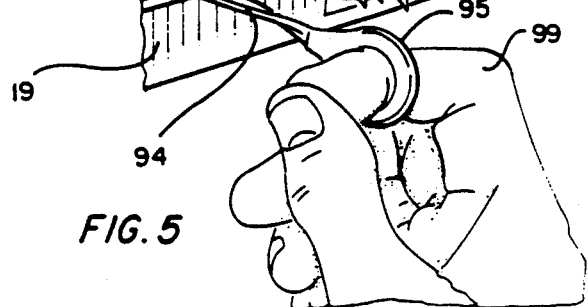
FIG. 5 is an isolated view, similar to FIG. 4, showing the use of the pull tab to separate the halves of the central package during use.

As shown in FIGS. 3-5, the upper and lower halves 17, 19 of the central package 13 can be assembled by means of a sealant ribbon 89 having an internal filament 94 and opposing ends 91, 93 which are joined at a pull tab 95. The sealant ribbon can be provided with a suitable adhesive on the upper and lower surfaces thereof for joining the peripheral lip regions 41, 42 of the upper and lower halves 17, 19 of the central package. The pull tab 95 is conveniently located within a side pocket 97 which allows the user's finger 99 to grasp the tab and pull the filament 94 around the periphery of the container halves to separate the halves during use. Any of a number of adhesive sealants can be utilized on the surfaces of the sealant ribbon 89 which will be familiar to those skilled in the art and which form permanent hermetic seals but which will unseal by pulling tab 95. Such adhesive sealants include, for example, pressure sensitive resin adhesives, thermosetting adhesives, and curable resin adhesive mixtures. Such adhesive sealants and the method of employment are generally well known and will not be described in further detail.

As shown in FIGS. 1 and 2, the central package upper half 17 includes a connecting means, such as pins 101 which run along a portion of the lip region 42 and which are engaged within mating pin receiving openings 103 provided in a molded synthetic handle 105. As shown in FIG. 1, the handle 105 is provided with a handle opening 107 for convenience in transporting the modular packaging system 11. The handle opening 107 can also be selectively sized to receive an outwardly extending projection, such as pegs 109, 111 extending from a vertically oriented storage panel 113. In this way, a plurality of modular packaging systems, such as systems 115, 117 can be arranged on the storage panel 113 for convenient access during surgical procedures.

In operation, a first type of sterilizable item or items are placed within the initially open interior 15 of the central package 13 and sterilized, as by exposure to GAMMA irradiation, the package halves being joined by the sealant ribbon 89 to form a bacteria barrier. A second and diverse type of sterilizable item, such as those requiring sterilization by steam, is carried within an accessory module and installed within an accessory receiving compartment formed in the external sidewalls of the central package. The accessory receiving module can be retained within the compartment by a suitable adhesive applied between the module and compartment or by enclosing the module with a surrounding package wrapping.

An invention has been provided with several advantages. The packaging system of the invention provides a more convenient, compact and secure system for packaging surgical products, such as the products utilized during ophthalmic surgery. The modular packaging system of the invention is easier for operating room personnel to open and disassemble. The packaging system of the invention provides convenient storage, since the containers can be stacked easily. The package construction also serves to protect the contents of the container from physical damage due to impact during shipping or other handling.

The outer walls of the core package of the packaging system of the invention reduce the tendency for the container contents to shift during use or transit, thereby decreasing the consequent disorganization of the contents of the container such as might occur when a flexible plastic bag is utilized to contain surgical products. The packaging system of the invention is easier for operating room personnel to disassemble and locate particular components required during a given surgical procedure. The modular nature of the package, and particularly the external compartments formed in the external sidewalls of the central package allow for a safer and more versatile method of piggybacking than was previously possible. The use of external piggyback compartments allows a variety of surgical items to be stored in associated fashion in a module packaging system, even where the items require sterilization by diverse means. The modular packaging system is well adapted for storage on a vertical rack, whereby a number of accessory packages can be conveniently stored and arranged for immediate use in the hospital environment.

While the invention has been shown in only one of its forms, it is not thus limited but is susceptible to various changes and modifications without departing from the spirit thereof.

What is claimed is:

1. A modular surgical packaging system for packaging sterile surgical items utilized during ophthalmic surgical procedures requiring sterilization by diverse means, the packaging system comprising:

a central package having an initially open interior for containing surgical items sterilizable by a first means of sterilization, and having external sidewalls including a top surface, a bottom surface, and connecting sidewalls formed of a relatively rigid material, said package having an open top half and an open bottom half, each of said open top half and said open bottom half having a mating peripheral lip, the mating peripheral lips being joined by seal means when the top half and the bottom half are assembled to form the central package, said seal means comprising a sealant ribbon having adhesive top and bottom surfaces for joining the mating peripheral lips of the central package halves, the sealant ribbon also containing a pullable filament which is connected to a pull tab, whereby pulling the pull tab severs the sealant ribbon and frees the package halves during use;

at least one recessed compartment integrally formed in the external sidewalls of the central package; and a piggyback module for containing surgical items sterilizable by a second and diverse means of sterilization received within the recessed compartment integrally formed on the external sidewalls of the central package.

2. A modular surgical packaging system for packaging sterile surgical items utilized during ophthalmic surgical procedures requiring sterilization by diverse means, the packaging system comprising:

a central package having external sidewalls including a top surface, a bottom surface, and connecting sidewalls formed of a relatively rigid material, said package having an initially open interior for containing surgical items sterilizable by a first means of sterilization;

at least one recessed compartment, said compartment having generally vertically extending sidewalls extending downwardly from the plane of the top surface of the central package, the vertically extending sidewalls being connected by a sloped floor which forms a generally triangular indentation in the external sidewalls of the central package when viewed in cross-section; and a piggyback module for containing surgical items sterilizable by a second and diverse means of sterilization received within the recessed compartment integrally formed on the external sidewalls of the central packages, said piggyback module having a generally triangular external configuration which conforms to the shape of the external sidewalls of the central package when the module is received within the triangular indentation.

3. A modular surgical packaging system for packaging sterile surgical items utilized during ophthalmic surgical procedures requiring sterilization by diverse means, the packaging system comprising:

a central package having external sidewalls including a top surface, a bottom surface, and connecting sidewalls formed of a relatively rigid material, said package having an initially open interior for containing surgical items sterilizable by a first means of sterilization;

at least one recessed compartment, said compartment having generally vertically extending sidewalls extending downwardly from the plane of the top surface of the central package, the vertically extending sidewalls being connected by an arcuate floor region; and a piggyback module for containing surgical items sterilizable by a second and diverse means of sterilization received within the recessed compartment integrally formed on the external sidewalls of the central packages, said piggyback module including a cylindrical sleeve for holding a liquid pharmaceutical product, the cylindrical sleeve being selectively sized to be received within the arcuate floor region of the recessed compartment in complimentary fashion.

4. The modular surgical packaging system of claim 3, wherein the piggyback module further comprises a planar exterior portion which encloses the sleeve within the recessed compartment of the central package, the planar exterior portion being foldable along a central axis to form a first planar fold which lies generally in the plane of the top surface of the central package and which forms a second planar fold which conforms generally to the shape of the remaining external sidewalls of the central container when the module is received within the recessed compartment.

5. The modular surgical packaging system of claim 2, wherein the central package includes a handle having a handle opening, the handle opening being selectively sized to receive an outwardly extending projection extending from a vertically oriented storage panel, whereby a plurality of central packages can be arranged on the storage panel for access during surgical procedures.

* * * * *